United States Patent [19]

Boehner et al.

[11] 4,035,487
[45] July 12, 1977

[54] PESTICIDAL 2-PHENYL-1,2,3-TRIAZOLYL-(4) AND-TRIAZOX-(1)-YL-(4) PHOSPHATE AND THIOSPHOSPHATE ESTERS

[75] Inventors: Beat Boehner, Binningen; Dag Dawes, Pratteln; Haukur Kristinsson, Bottmingen; Willy Meyer, Basel, all of Switzerland

[73] Assignee: Ciba-Geigy Corporation, Ardsley, N.Y.

[21] Appl. No.: 555,009

[22] Filed: Mar. 3, 1975

Related U.S. Application Data

[63] Continuation-in-part of Ser. No. 501,393, Aug. 28, 1974, abandoned.

[30] Foreign Application Priority Data

July 24, 1974 Switzerland ............ 10210/74
Sept. 10, 1973 Switzerland ............ 12961/73

[51] Int. Cl.² .................. C07D 249/06; A01N 9/36
[52] U.S. Cl. ........................ 424/200; 260/308 A; 260/465 E; 260/471 R; 260/566 A
[58] Field of Search ................. 260/308 A; 424/200

[56] References Cited

U.S. PATENT DOCUMENTS 3,216,894  11/1965  Lorenz et al. ................ 260/308 A

FOREIGN PATENT DOCUMENTS 713,278  8/1954  United Kingdom ........... 260/308 A

*Primary Examiner*—Raymond V. Rush
*Attorney, Agent, or Firm*—Frederick H. Rabin

[57] ABSTRACT

1,2,3-Triazolyl phosphorus compounds, their manufacture and use as active ingredients for controlling insects, representatives of the order acarina and phytopathogenic nematodes. The compounds correspond to the formula

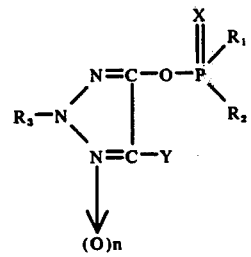

wherein
$R_1$ represents alkyl, alkoxy, alkylthio, alkoxyalkylthio, amino, monoalkylamino or dialkylamino,
$R_2$ represents alkoxy, alkylthio, amino, monoalkylamino or dialkylamino,
$R_3$ represents unsubstituted or substituted phenyl,
Y represents hydrogen, chlorine or bromine,
$n$ represents the numbers 0 or 1, and
X represents oxygen or sulphur.

32 Claims, No Drawings

PESTICIDAL 2-PHENYL-1,2,3-TRIAZOLYL-(4) AND-TRIAZOX-(1)-YL-(4) PHOSPHATE AND THIOSPHOSPHATE ESTERS

CROSS REFERENCES

This is a continuation in part of application Ser. No. 501,393, filed Aug. 28, 1974 now abandoned.

The present invention relates to 1,2,3-triazolyl compounds, to processes for their preparation and to their use for the control of pests.

The said 1,2,3-triazolyl compounds correspond to the formula

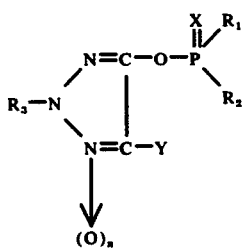

wherein
$R_1$ represents alkyl, alkoxy, alkylthio, alkoxyalkylthio, amino, monoalkylamino or dialkylamino,
$R_2$ represents alkoxy, alkylthio, amino, monoalkylamino or dialkylamino,
$R_3$ represents unsubstituted or substituted phenyl,
Y represents hydrogen, chlorine or bromine,
n represents the numbers 0 or 1, and
X represents oxygen or sulphur.

The alkyl, alkylamino, dialkylamino, alkoxy, alkylthio and alkoxyalkylthio groups denoted by $R_1$ and $R_2$ can be branched-chain or straight-chain, substituted or unsubstituted, and they have 1 to 18, especially, however, 1 to 5, cabon atoms in the chain. Substituents on these groups are preferably: fluorine, chlorine, methoxy, methylthio and/or nitro. Examples of such groups are, inter alia: methyl, methoxy, ethyl, ethoxy, ethylthio, methylamino, dimethylamino, methoxymethylthio, methoxyethylthio, ethoxyethylthio, n-propyl, n-propoxy, n-propylthio, isopropyl, isopropoxy, isopropylthio, n-, i-, sec.-, tert.-butyl, n-pentyl and isomers thereof, n-pentoxy, n-pentylthio and chloromethyl.

Substituents of the phenyl groups in the case of $R_3$ are, for example, one or more identical or different fluorine, chlorine, bromine and/or iodine atoms, alkyl, haloalkyl, cyano, alkoxy, nitro, alkoxycarbonyl, alkylthio, alkylsulphonyl, alkylsulphinyl, acetylamino, amino, monoalkylamino, dialkylamino, phenoxy and/or phenylsulphonyl groups.

Compounds of formula I which are preferred on account of their action are those wherein
$R_1$ represents $C_1$-$C_5$-alkyl, $C_1$-$C_5$-alkoxy, $C_3$-$C_5$-alkylthio, methylamino or dimethylamino,
$R_2$ represents $C_1$-$C_5$-alkoxy or dimethylamino,
$R_3$ represents unsubstituted phenyl, or phenyl mono- to trisubstituted, identically or differently, by fluorine, chlorine, bromine and/or iodine, or monosubstituted by methyl, methoxy or trifluoromethyl,
Y represents hydrogen, chlorine or bromine,
n represents the numbers 0 or 1, and
X represents oxygen or sulphur.

Particularly preferred compounds of formula I are those wherein
$R_1$ represents methyl, ethyl, methoxy, ethoxy, $C_3$-$C_5$-alkylthio, methylamino or dimethylamino,
$R_2$ represents methoxy, ethoxy or dimethylamino,
$R_3$ represents unsubstituted phenyl, or phenyl mono- to trisubstituted by fluorine, chlorine and/or bromine or monosubstituted by methyl, methoxy or trifluoromethyl,
Y represents hydrogen, chlorine or bromine,
n represents the numbers 0 or 1, and
X represents oxygen or sulphur.

More especially preferred compounds of formula I are those wherein
$R_1$ represents methoxy, ethoxy or n-propylthio,
$R_2$ represents methoxy or ethoxy,
$R_3$ represents unsubstituted phenyl, or phenyl mono- to trisubstituted by fluorine, chlorine and/or bromine or monosubstituted by methyl, methoxy or trifluoromethyl,
Y represents hydrogen, chlorine or bromine,
n represents the numbers 0 or 1, and
X represents sulphur.

The compounds of formula I can be prepared by the following methods known per se:

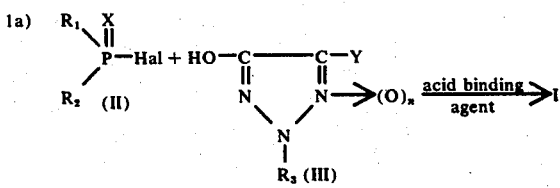

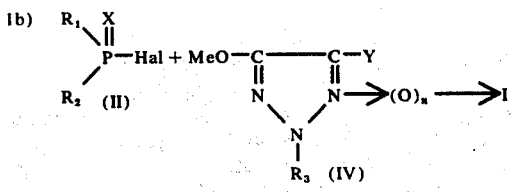

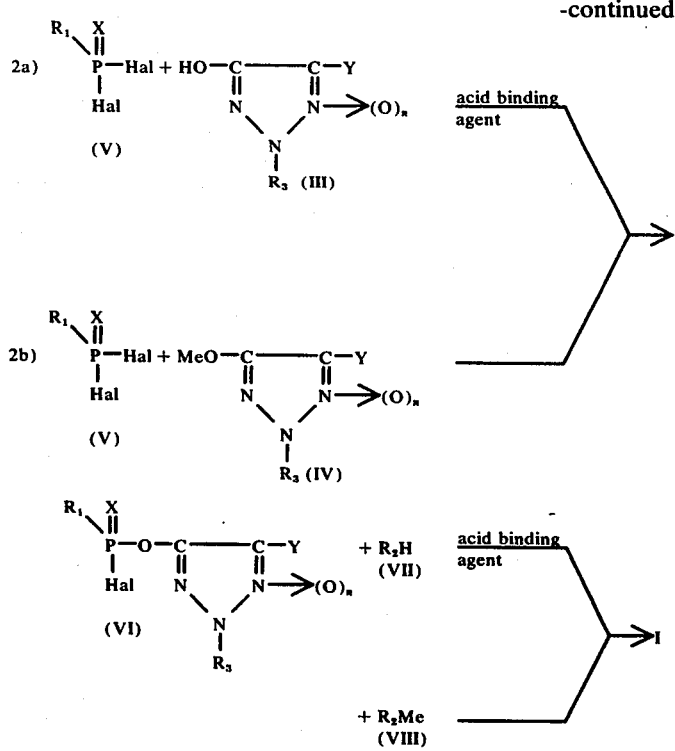

In formulae II to VIII, the symbols $R_1$ to $R_3$, X, Y and n have the meanings given for formula I, Hal stands for fluorine, chlorine, bromine or iodine, particularly, however, for fluorine, chlorine or bromine, $R'_2$ stands for alkoxy or alkylthio, and Me denotes a monovalent metal, preferably an alkali metal, especially sodium or potassium. Suitable acid-binding agents are, for example, the following bases: tertiary amines such as triethylamine, dimethylaniline and pyridine, inorganic bases such as hydroxides and carbonates of alkali metals and alkaline-earth metals, preferably sodium and potassium carbonate. The reactions 1a, 1b, 2a and 2b are performed under normal pressure, at a temperature of 0°–150° C, and preferably in solvents or diluents which are inert to the reactants. Suitable solvents or diluents are, for example: aromatic hydrocarbons such as benzene, toluene and ligroins; halogenated hydrocarbons such as chlorobenzene, polychlorobenzenes and bromobenzene; chlorinated alkanes having 1 to 3 carbon atoms; ethers such as dioxane and tetrahydrofuran; esters such as acetic acid ethyl ester; ketones such as methyl ethyl ketone and diethyl ketone; and nitriles, etc.

Of the compounds of formula III or IV to be used as starting materials, only 2-phenyl-4-hydroxy-1,2,3-triazole is known. This is preferred by firstly converting glyoxal, by reaction with phenylhydrazine, into glyoxaldiphenylhydrazone, and condensing this in the presence of copper sulphate to 2-phenyl-1,2,3-triazole (see J. L. Riebsomer, J. Org. Chem. 13, (1948), 815). This is then converted with fluorosulphonic acid methyl ester into 2-phenyl-3-methyl-1,2,3-triazolium fluorosulphonate, which yields, by treatment with N-bromosuccinimide and sodium hydroxide solution, 2-phenyl-3-methyl-1,2,3-triazolin-4-one (see M. Begtrup et al., Acta Chem. Scand, 25, (1971) 2097). The last-mentioned compound is subsequently converted by reaction with benzoyl chloride into 2-phenyl-4-benzoyloxy-1,2,3-triazole, which yields, with alkaline hydrolysis, 2-phenyl-4-hydroxy-1,2,3-triazole (see M. Begtrup, Acta Chem. Scand. 26, (1972), 715). By an analogous process, it is possible to prepare further compounds of formula III, which are substituted in the phenyl radical according to the above definition for the radical $R_3$, starting with correspondingly substituted phenylhydrazines. The compounds thus obtained can be chlorinated or brominated in the 4-position. The introduction of chlorine or bromine in the 4-position is effected by the action of elementary chlorine or bromine in solvents inert to these agents, such as halogenated hydrocarbons. Furthermore, N-chlorosuccinimide and N-bromosuccinimide are suitable for the introduction of chlorine and bromine, respectively. With the use of these halogenating agents, the procedure is carried out in the aforementioned halogenated hydrocarbons, particularly in carbon tetrachloride.

The compounds of formula III in which n is 0 obtained in this manner can in addition be converted in the usual manner by the action of hydrogen peroxide or organic peroxy acids, such as peroxybenzoic acid or m-chloroperoxybenzoic acid, in glacial acetic acid into the corresponding 1-oxides.

The starting compounds of the general formula III in which n is 1 and Y is hydrogen can also be advantageously prepared by heating an oxime-hydrazone of the formula

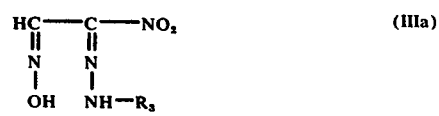

in the presence of a lower aliphatic acid at temperatures between about 15° to 100° C.

The compounds of formula I have a broad biocidal action, and can be used for the control of various animal and plant pests. They are particularly suitable for the control of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae; as well as acarids of the families: Ixodidae, Argasidae, Tetranychidae and Dermanyssidae. Especially advantageous is their use against eating insects. Some compounds of formula I are also suitable for the control of phytopathogenic nematodes.

The insecticidal and acaricidal action can be appreciably broadened and adapted to suit given circumstances by the addition of other insecticides and/or acaricides. Suitable additives are, for example, organic phosphorus compounds, nitrophenols and derivatives thereof, formamidines, ureas, pyrethrin-like compounds, carbamates or chlorinated hydrocarbons.

The compounds of formula I can be used on their own or together with suitable carriers and/or additives. Suitable carriers and additives may be solid or liquid, and they correspond to the substances common in formulation practice, such as, for example, natural or regenerated substances, solvents, dispersing agents, wetting agents, adhesives, thickeners, binders and/or fertilizers.

For application, the compounds of formula I can be processed into the form of dusts, emulsion concentrates, granulates, dispersions, sprays or solutions, the formulation of these preparations being effected in a manner commonly known in practice.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

SOLID PREPARATIONS dusts, scattering agents, granulates, coated granulates, impregnated granulates and homogeneous granulates;

LIQUID PREPARATIONS a. water-dispersible active-substance concentrates: wettable powders, pastes or emulsions;
b. solutions.

The content of active substance in the described agents is between 0.1 and 95%.

The active substances of formula I can be formulated, for example, as follows:

DUSTS

The following substances are used in the preparation of (a) a 5% dust, and (b) a 2% dust:
a. 5 parts of active substance,
   95 parts of talcum;
b. 2 parts of active substance,
   1 part of highly dispersed silicic acid,
   97 parts of talcum.

The active substance are mixed and ground with the carriers.

GRANULATE

The following substances are used to prepare a 5% granulate:
5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed onto kaolin, and the actone subsequently evaporated off in vacuo.

WETTABLE POWDER

The following constituents are used for the preparation of (a) a 40%, (b) and (c) a 25%, and (d) a 10% wettable powder:
a. 40 parts of active substance,
   5 parts of sodium lignin sulphonate,
   1 part of sodium dibutyl-naphthalene sulphonate,
   54 parts of silicic acid;
b. 25 parts of active substance,
   4.5 parts of calcium lignin sulphonate,
   1.9 parts of Champagne chalk/hydroxyethyl cellulose mixture (1:1),
   1.5 parts of sodium dibutyl naphthalene sulphonate,
   19.5 parts of silicic acid,
   19.5 parts of Champagne chalk,
   28.1 parts of kaolin,
c. 25 parts of active substance,
   2.5 parts of isooctylphenoxy-polyoxyethylene-ethanol,
   1.7 parts of Champagne chalk/hydroxyethyl cellulose mixture (1:1),
   8.3 parts of sodium aluminum silicate,
   16.5 parts of kieselguhr,
   46 parts of kaolin;
d. 10 parts of active substance,
   3 parts of a mixture of the sodium salts of saturated of naphthalenesulphonic acid/formaldehyde condensate,
   82 parts of kaolin.

The active substances are intimately mixed, in suitable mixers, with the additives, and the mixture is subsequently ground in the appropriate mills and rollers. Wettable powders are obtained which can be diluted with water to give suspensions of any desired concentration.

EMULSIFIABLE CONCENTRATES

The following substances are used to prepare (a) a 10%, (b) a 25% and (c) a 50% enmulsifiable concentrate:
a. 10 parts of active substance,
   3.4 parts of epoxidised vegetable oil,
   3.4 parts of a combination emulsifier consisting of fatty alcohol polyglycol ether and alkylarylsulphonate calcium salt,
   40 parts of dimethylformamide,
   43.2 parts of xylene;
b. 25 parts of active substance,
   2.5 parts of epoxidised vegetable oil,
   10 parts of an alkylarylsulphonate/fatty alcohol polyglycol ether mixture,
   5 parts of dimethylformamide, 57.5 parts of xylene.
c. 50 parts of active substance
   4.2 parts of tributylphenol-polyglycolether
   5.8 parts of calcium dodecylbenzenesulfonate
   20 parts of cyclohexanone
   20 parts of xylene From these concentrates it is possible to prepare, by dilution with water, emulsions of any desired concentration.

SPRAY

The following constituents are used to prepare a 5% spray:
5 parts of active substance,
1 part of epichlorhydrin,
94 parts of ligroin (boiling limits 160°–190° C).

AGENT FOR THE ULTRA LOW VOLUME SPRAYING TECHNIQUE 95 parts of active substance,
5 parts of epichlorohydrin.

EXAMPLE 1

A. Preparation of O,O-diethyl-O-[2-p-chlorophenyl-1,2,3-triazox-(1)-yl-(4)]-thiophosphate 12 ml of triethylamine is added dropwise to a solution of 21.1 g of 2-p-chlorophenyl-4-hydroxy-1,2,3-triazole-1-oxide and 19.0 g of diethylthiophosphoric acid chloride in 300 ml of acetonitrile. After 6 hours' refluxing, the reaction mixture is cooled to room temperature, and the formed triethylamine hydrochloride is filtered off. The filtrate is concentrated in vacuo, and subsequently extracted by shaking with ether/water. The ether phase is separated, and dried with sodium sulphate. After removal of the drying agent, the ether is distilled off. The residue is purified through silica gel with 5% of methanol in chloroform as the eluant.

The eluant is distilled off to obtain the compound of the formula

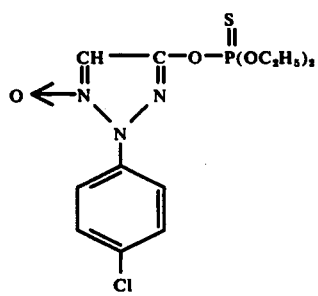

in the form of oil having a refractive index of $n_D^{20} = 1.5728$.

B. Preparation of O,O-diethyl-O-[2-phenyl-1,2,3-triazolyl-(4)]-thiophosphate 16.1 g of 2-phenyl-4-hydroxy-1,2,3-triazole and 18.9 g of diethylthiophosphoric acid chloride are refluxed with 13.8 ml of triethylamine in 300 ml of acetonitrile for 5 hours. The reaction mixture is cooled to room temperature and triethylamine hydrochloride is filtered off. The filtrate is concentrated in vacuo, and subsequently extracted with ether/water. The ether phase is separated, and dried with sodium sulphate. After removal of the drying agent, the ether is distilled off. The residue is purified through silica gel with chloroform as the eluant. The eluant is distilled off to obtain the compound of the formula

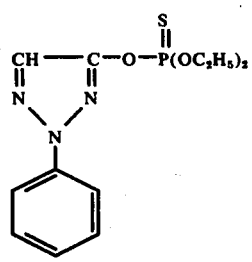

in the form of yellow oil having a refractive index of $n_D^{20} = 1.5480$.

The following compounds are prepared in an analogous manner:

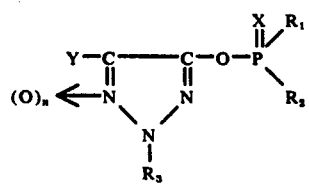

| $R_1$ | $R_2$ | $R_3$ | X | Y | n = the number | Physical data |
|---|---|---|---|---|---|---|
| —OC$_2$H$_5$ | —OC$_2$H$_5$ | —C$_6$H$_5$ | S | H | 1 | $n_D^{20}$ : 1,563 |
| —N(CH$_3$)$_2$ | —N(CH$_3$)$_2$ | —C$_6$H$_5$ | O | H | 0 | $n_D^{20}$ : 1,6689 |
| —OCH$_3$ | —OCH$_3$ | —C$_6$H$_5$ | S | H | 1 | $n_D^{20}$ : 1,5765 |
| —SC$_3$H$_7$(n) | —OC$_2$H$_5$ | —C$_6$H$_5$ | S | H | 1 | $n_D^{20}$ : 1,590 |
| —SC$_3$H$_7$(n) | —OC$_2$H$_5$ | —C$_6$H$_5$ | S | H | 0 | $n_D^{20}$ : 1,5800 |
| —NHCH$_3$ | —OC$_2$H$_5$ | —C$_6$H$_5$ | S | H | 1 | $n_D^{20}$ : 1,5720 |

-continued

| R₁ | R₂ | R₃ | X | Y | n = the number | Physical data |
|---|---|---|---|---|---|---|
| —OC₂H₅ | —OC₂H₅ | 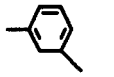 CF₃ | S | H | 1 | $n_D^{20}$ : 1,5171 |
| —OC₂H₅ | —OC₂H₅ |  Cl | S | H | 1 | $n_D^{20}$ : 1,5753 |
| —OC₂H₅ | —OC₂H₅ | 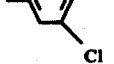 Cl | S | H | 1 | $n_D^{20}$ : 1,6625 |
| —OC₂H₅ | —OC₂H₅ |  Cl, Cl | S | H | 1 | M.P. : 56–57° C |
| —OC₂H₅ | —OC₂H₅ | 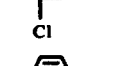 | S | Cl | 0 | $n_D^{20}$ : 1,5552 |
| —OC₂H₅ | —OC₂H₅ | 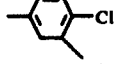 | S | Br | 0 | $n_D^{20}$ : 1,5667 |
| —SC₃H₇(n) | —OC₂H₅ | 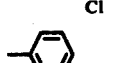 Cl | S | H | 1 | $n_D^{20}$ : 1,5894 |
| —SC₃H₇(n) | —OC₂H₅ | 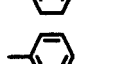 Cl | S | H | 1 | $n_D^{20}$ : 1,6043 |
| —OC₂H₅ | —OC₂H₅ | 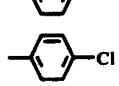 CH₃ | S | H | 1 | $n_D^{20}$ : 1,5509 |
| —OC₂H₅ | —OC₂H₅ |  CH₃ | S | H | 1 | $n_D^{20}$ : 1,5629 |
| —OC₂H₅ | —OC₂H₅ | 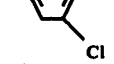 OCH₃ | S | H | 1 | $n_D^{20}$ : 1,5542 |
| —OC₂H₅ | —OC₂H₅ | 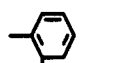 OCH₃ | S | H | 1 | $n_D^{20}$ : 1,5634 |
| —OC₂H₅ | —OC₂H₅ | 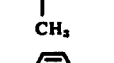 Br | S | H | 1 | M.P.:60–63° C |
| —OC₂H₅ | —OC₂H₅ | 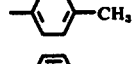 F | S | H | 1 | $n_D^{20}$ : 1,5511 |
| —C₂H₅ | —OC₂H₅ | 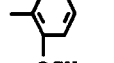 Cl | S | H | 1 | $n_D^{20}$ : 1,5709 |
| —OC₂H₅ | —OC₂H₅ | 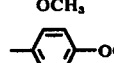 F | S | H | 1 | $n_D^{20}$ : 1,5558 |
| —OCH₃ | —OCH₃ | 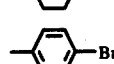 | S | H | 0 | |
| —C₂H₅ | —OC₂H₅ | 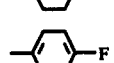 | S | H | 1 | |
| —C₂H₅ | —OC₂H₅ | 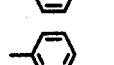 | S | H | 0 | |
| —NHCH₃ | —OC₂H₅ | 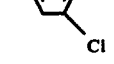 | S | H | 0 | |
| —OC₂H₅ | —OC₂H₅ | 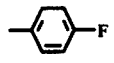 | O | H | 1 | |
| —OC₂H₅ | —OC₂H₅ | 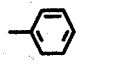 | O | H | 0 | |

-continued

| R₁ | R₂ | R₃ | X | Y | n = the number | Physical data |
|---|---|---|---|---|---|---|
| —SC₃H₇(n) | —OC₂H₅ |  | O | H | 1 | |
| —SC₃H₇(n) | —OC₂H₅ |  | O | H | 0 | |
| —OC₂H₅ | —OC₂H₅ |  | S | H | 0 | |
| OC₂H₅ | —OC₂H₅ |  | S | H | 0 | |
| —OC₂H₅ | —OC₂H₅ |  | S | H | 0 | |
| —OC₂H₅ | —OC₂H₅ |  | S | H | 0 | |
| —OC₂H₅ | —OC₂H₅ |  | S | Br | 1 | |
| —OC₂H₅ | —OC₂H₅ |  | S | Cl | 1 | |
| —OC₂H₅ | —OC₂H₅ |  | S | H | 1 | |
| —OC₂H₅ | —OC₂H₅ |  | S | H | 1 | |
| —OC₂H₅ | —OC₂H₅ |  | S | H | 1 | |

EXAMPLE 2

Insecticidal Stomach Poison Action

Cotton and ptato plants were sprayed with a 0.05% aqueous active-substance emulsion (obtained from a 10% emulsifiable concentrate).

After the drying of the resulting coating, *Spodoptera littoralis* or *Heliothis virescens* larvae L₃ were placed onto the cotton plants, and Colorada beetle larvae (*Leptinotarsa decemlineata*) onto the potato plants. The test was carried out at 24° C with 60% relative humidity.

The compounds according to Example 1 exhibited in the above test a good insecticidal stomach poison action against *Spodptera littoralis*, *Heliothis virescens* and *Leptinotarsa decemlineata* larvae.

EXAMPLE 3

Action against *Chilo suppressalis*

Rice plants of the type Caloro were planted, six plants per pot, in plastic pots having a top diameter of 17 cm, and grown to a height of about 60 cm. Infestation with *Chilo suppressalis* larvae (L₁; 3–4 mm long) was carried out 2 days after application of the active substance in granular form (amount applied = 8 kg of active substance per hectare) to the paddy water. The evaluation of the insecticidal action was made 10 days after application of the granules.

The compounds according to Example 1 were effective against *Chilo suppressalis* in the above test.

EXAMPLE 4

Action against ticks

A. *Rhipicephalus bursa*

In each case, 5 adult ticks or 50 tick larvae were placed into a small glass test tube, and subsequently immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks, and in the case of the larvae after 2 days. There were two repeats for each test.

B. *Boophilus microplus* (larvae)

With a dilution series analogous to that in Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

EXAMPLE 5

Acaricidal Action

*Phaseolus vulgaris* (plants) were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no running-off of the spray liquor. An assessment was made after 2 to 7 days, by examination under a binocular, of the living and of the dead larvae, adults and eggs, and the results were expressed as percentages. The treated plants were kept during the "holding time" in greenhouse compartments at 25° C.

The compounds according to Example 1 were effective in the above test against adults, larvae and eggs of *Tetranychus urticae*.

EXAMPLE 6

Action against Soil Nematodes

In order to test the action against soil nematodes, the active substances were added, in the concentration stated in each case, to soil infested with root-gall-nematodes (*Meloidogyne arenaria*); the whole was then intimately mixed. In the one test series, tomato seedlings were planted immediately after preparation of the soil in this manner, and in the other test series tomatoes were planted after a waiting time of 8 days.

For an assessment of the nematocidal action, the galls present on the roots were counted 28 days after planting and sowing, respectively.

Some active substances according to Example 1 exhibited in this test a good action against *Meloidogyne arenaria*.

What we claim is:
1. A compound of the formula

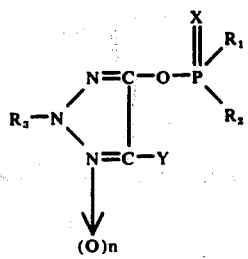

wherein
$R_1$ represents methyl, ethyl, methoxy, ethoxy, $C_3$-$C_5$-alkylthio, methylamino or dimethylamino,
$R_2$ represents methoxy, ethoxy or dimethylamino,
$R_3$ represents unsubstituted phenyl, or phenyl mono- to trisubstituted by fluorine, chlorine and/or bromine, or monosubstituted by methyl, methoxy or trifluoromethyl,
Y represents hydrogen, chlorine or bromine,
n represents the numbers 0 or 1, and
X represents oxygen or sulphur.
2. A compound according to claim 1 wherein
$R_1$ represents methoxy, ethoxy or n-propylthio,
$R_2$ represents methoxy or ethoxy;

X represents sulphur.
3. Compound according to claim 2 of the formula

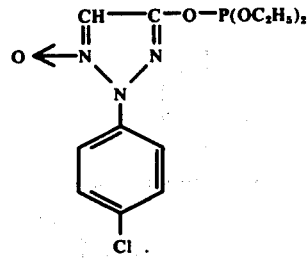

4. Compound according to claim 2 of the formula

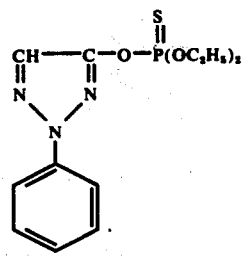

5. Compound according to claim 2 of the formula

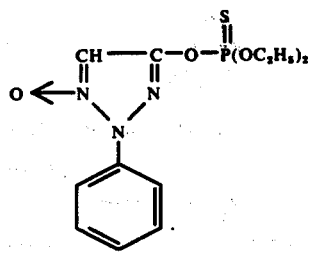

6. Compound according to claim 1 of the formula

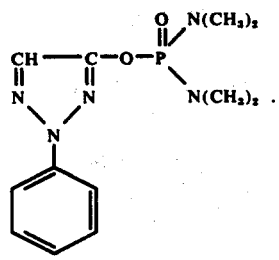

7. Compound according to claim 2 of the formula

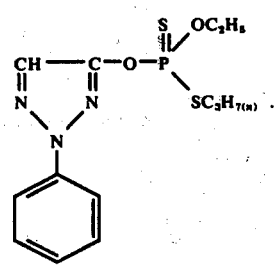

8. Compound according to claim 2 of the formula

9. Compound according to claim 2 of the formula

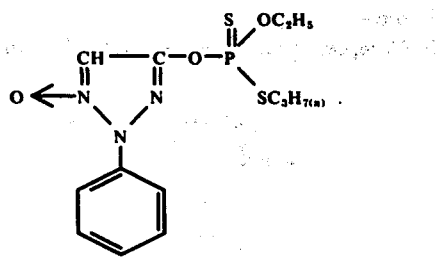

10. Compound according to claim 2 of the formula

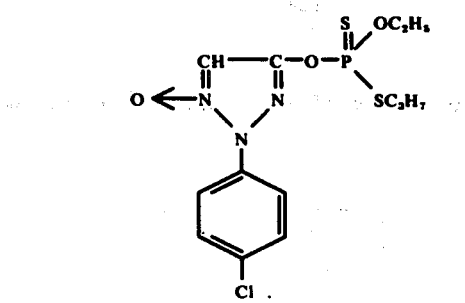

11. Compound according to claim 2 of the formula

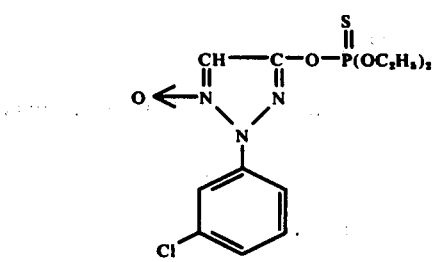

12. Compound according to claim 2 of the formula

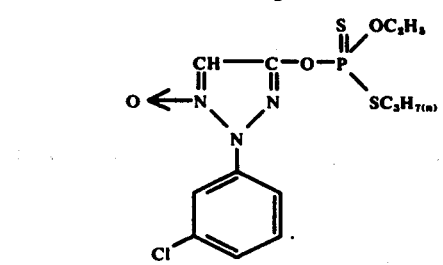

13. Compound according to claim 2 of the formula

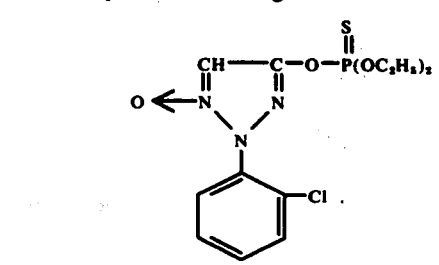

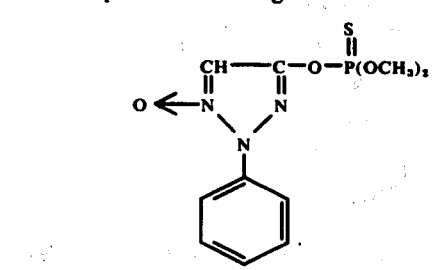

14. Compound according to claim 2 of the formula

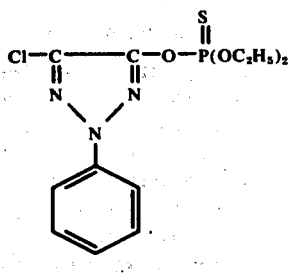

15. Compound according to claim 2 of the formula

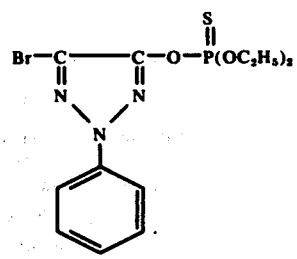

16. Compound according to claim 2 of the formula

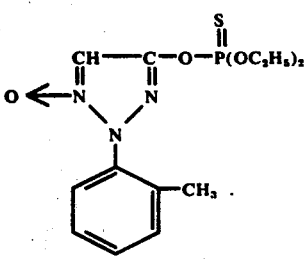

17. Compound according to claim 2 of the formula

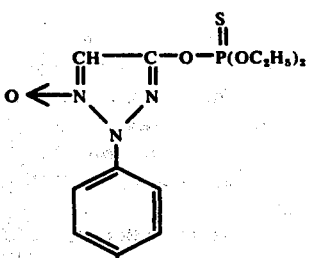

18. Compound according to claim 2 of the formula

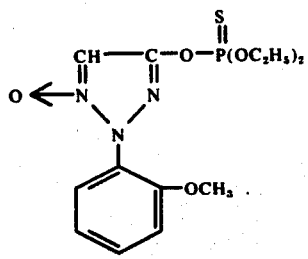

19. Compound according to claim 2 of the formula

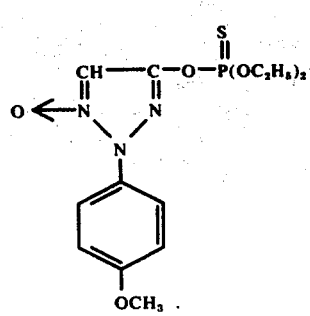

20. Compound according to claim 2 of the formula

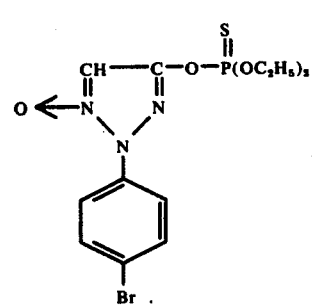

21. Compound according to claim 2 of the formula

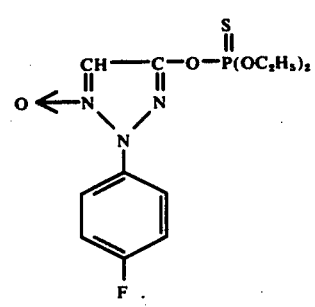

22. Compound according to claim 1 of the formula

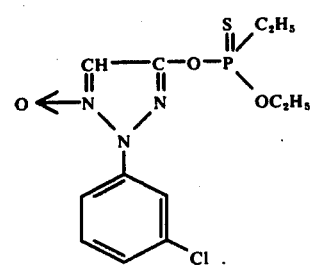

23. Compound according to claim 2 of the formula

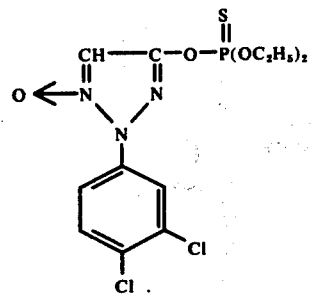

24. Compound according to claim 1 of the formula

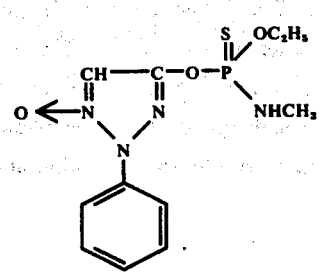

25. Compound according to claim 2 of the formula

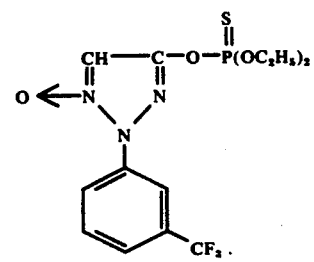

26. An insecticidal, acaricidal and nematocidal composition containing (1) as active component an effective amount of a compound of the formula

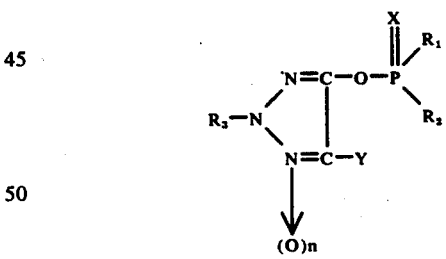

wherein
R$_1$ represents methyl, ethyl, methoxy, ethoxy, C$_3$–C$_5$ alkylthio, methylamine or dimethylamino,
R$_2$ represents methoxy, ethoxy or dimethylamino,
R$_3$ represents unsubstituted phenyl, or phenyl mono- to tri-substituted by fluorine, chlorine and/or bromine, or monosubstituted by methyl, methoxy or trifluoromethyl,
Y represents hydrogen, chlorine or bromine,
n represents the numbers 0 or 1, and
X represents oxygen or sulphur, and (2) a carrier.

27. A method for the control of insects, acarids and nematodes which comprises applying thereto an insecticidally, acaricidally or nematocidally effective amount of a compound of the formula

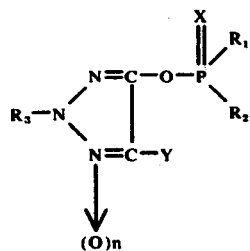

wherein $R_1$ represents methyl, ethyl, methoxy, ethoxy, $C_3$–$C_5$ alkylthio, methylamino or dimethylamino, $R_2$ represents methoxy, ethoxy, or dimethylamino, $R_3$ represents unsubstitued phenyl, or phenyl mono- to tri-substituted by fluorine, chlorine and/or bromine, or monosubstituted by methyl, methoxy or trifluoromethyl, Y represents hydrogen, chlorine or bromine, $n$ represents the numbers 0 or 1, and X represents oxygen or sulphur.

28. A method according to claim 27 wherein $R_1$ represents methoxy, ethoxy or n-propylthio; $R_2$ represents methoxy or ethoxy; and X represents sulphur.

29. A method according to claim 28 in which the compound is O,O-diethyl-O-[2-p-chlorophenyl-1,2,3-triazox-(1)-yl-(4)]-thiophosphate.

30. A method according to claim 28 in which the compound is O,O-diethyl-O-[2-m-chlorophenyl-1,2,3-triazox-(1)-yl-(4)]-thiophosphate.

31. A method according to claim 28 in which the compound is O,O-diethyl-O-[2-m-chlorophenyl-1,2,3-triazox-(2)-yl-(4)]-thiophosphate.

32. A method according to claim 28 in which the compound is O,O-diethyl-O-[2-p-fluorophenyl-1,2,3-triazox-(1)-yl-(4)]-thiophosphate.

* * * * *

UNITED STATES PATENT AND TRADEMARK OFFICE
CERTIFICATE OF CORRECTION

PATENT NO. : 4,035,487
DATED : July 12, 1977
INVENTOR(S) : Beat Boehner, Dag Dawes, Haukur Kristinsson & Willy Meyer It is certified that error appears in the above-identified patent and that said Letters Patent are hereby corrected as shown below:

In column 14, in Claim 3, the structural formula should appear as follows:

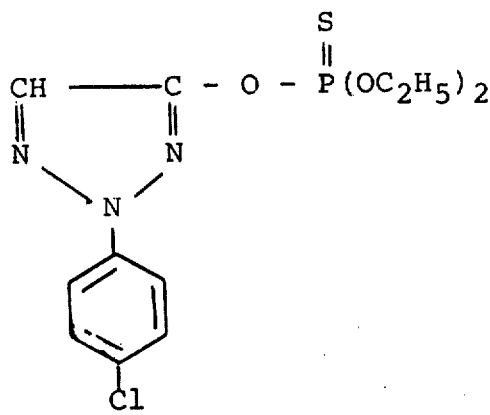

In column 18, Claim 26, line 56, the line should read:

alkylthio, methylamino or dimethylamino,

Signed and Sealed this

Eighteenth Day of October 1977

[SEAL]

Attest:

RUTH C. MASON
Attesting Officer

LUTRELLE F. PARKER
Acting Commissioner of Patents and Trademarks